United States Patent [19]

Slaugh et al.

[11] 4,453,015

[45] Jun. 5, 1984

[54] METHYL ETHYL KETONE PROCESS

[75] Inventors: Lynn H. Slaugh; Galeon W. Schoenthal; James D. Richardson, all of Houston, Tex.

[73] Assignee: Shell Oil Company, Houston, Tex.

[21] Appl. No.: 448,129

[22] Filed: Dec. 9, 1982

Related U.S. Application Data

[63] Continuation of Ser. No. 312,054, Oct. 16, 1981, abandoned.

[51] Int. Cl.³ .......................................... C07C 45/00
[52] U.S. Cl. .................................................. 568/406
[58] Field of Search ................................ 568/403, 406

[56] References Cited

U.S. PATENT DOCUMENTS 2,794,053 5/1957 Attheuter et al. .................. 568/403

FOREIGN PATENT DOCUMENTS

| 665376 | 1/1952 | United Kingdom | 568/403 |
| 817622 | 8/1959 | United Kingdom | 568/403 |
| 804132 | 11/1959 | United Kingdom | 568/403 |
| 938854 | 10/1963 | United Kingdom | 568/403 |

Primary Examiner—James H. Reamer

[57] ABSTRACT

Secondary butyl alcohol is dehydrogenated to methyl ethyl ketone by contact with a catalyst having improved selectivity and activity which comprises a mixture of copper, zinc and chromium supported on an alpha alumina carrier.

14 Claims, No Drawings

METHYL ETHYL KETONE PROCESS

This is a continuation of application Ser. No. 312,054, filed Oct. 16, 1981 now abandoned.

FIELD OF THE INVENTION

This invention relates to an improved process for converting secondary butyl alcohol to methyl ethyl ketone in the presence of catalyst comprising copper, zinc and chromium supported on an alpha alumina support.

BACKGROUND OF THE INVENTION

A large number of catalysts have been cited as useful in the continuous dehydrogenation of alcohols to ketones and aldehydes. Among them are metals such as copper, zinc, and brass and oxides such as zinc oxide, copper oxide, chromium oxide, chromium-promoted copper oxide, manganese oxide, magnesium oxide and others. See, for example, British Pat. No. 665,376 issued Jan. 23, 1952, British Pat. No. 804,132 issued Nov. 1958, British Pat. No. 817,622 issued Aug. 6, 1959, British Pat. No. 938,854 issued Oct. 9, 1963, and U.S. Pat. No. 2,794,053. The use of brass catalysts is old in the art, e.g., U.S. Pat. No. 1,952,702 issued Jan. 17, 1931.

SUMMARY OF THE INVENTION

This invention provides an improved process for the dehydrogenation, preferably in the vapor phase, of secondary butyl alcohol to methyl ethyl ketone in the presence of a catalyst comprising copper, zinc and chromium supported on an alpha alumina carrier. The use of the alpha alumina carrier provides a catalyst having improved selectivities over prior art catalysts, both unsupported catalysts and catalysts utilizing other supports. The instant catalyst, for example, provides a much more active catalyst than the commercially utilized brass spelter catalyst. Thus, the instant catalyst can be utilized at lower temperatures and/or at deeper conversions than is possible with the brass spelter catalyst. The use of an alpha alumina support provides for less by-product make than is obtained using other supports such as gamma alumina. The catalyst is prepared by impregnating the porous alpha alumina support with a solution(s) of copper, zinc and chromium salts, drying the impregnated support, calcining the support in an oxidizing atmosphere at a temperature ranging from about 100° C. to about 900° C. and then activating the calcined material in a reducing environment.

DESCRIPTION OF THE PREFERRED EMBODIMENTS

Basically, catalyst preparation comprises (1) impregnating a porous inert support with solutions of the requisite salts, (2) drying and calcining at a temperature ranging from about 100° C. to about 800° C. preferably from about 200° C. to about 700° C. and most preferably from about 300° C. to about 600° C., and (3) activating the calcined material in a reducing environment.

The carrier utilized in the catalyst of the invention is an alpha alumina, preferably of a macro porous structure, i.e., a structure having a B.E.T. surface area between about 0.01 to about 100 m$^2$/g, more preferably between about 0.05 to about 50 m$^2$/g and an apparent porosity as measured by conventional mercury or water adsorption techniques of from about 10% to about 50% by volume. The B.E.T. method for determining specific surface area is described in detail in Brunauer, S., Emmet, P. H., and Teller, E., J. Am. Chem. Soc., 60, 309–16 (1938). Other carriers such as gamma alumina, silica and silica-alumina provide a much less active catalyst.

The first step in the preparation of the catalyst is to impregnate the support with solubilized salts of copper, zinc and chromium. The salts must be soluble in a suitable solubilizing media, either organic or inorganic. Water is a preferred solubilizing media. Lower alkanols also provide examples of suitable organic solvents. Suitable metal salts are for example, chlorides, bromides, nitrates, acetates, lactates and the like. The impregnation of the support may be carried out in one step utilizing all three metals dissolved in a solution, or it may be carried out in a multi-step process, using one or more of the metals dissolved in individual impregnating steps. A preferred impregnating process is the so-called "dry impregnation" where just a sufficient amount of impregnating solution is used such that all the pore volume in the carrier is filled and no excess solution is left after impregnation. The next step is to dry and calcine the impregnated material. The drying and calcining can be carried out at temperatures up to about 150° C. followed by a calcining step at temperatures ranging from about 100° C. to about 900° C. preferably from about 300° C. to about 800° C. Preferably, the drying and calcining are carried out in one continuous step, heating the material slowly through the low temperature ranges to dry the material and then raising the temperature to the calcining conditions. The purpose of the calcining is to convert the soluble metal salts to oxides upon the support material. Calcining is carried out in a neutral or oxidizing atmosphere, air being the preferred atmosphere. Nitrogen is also a suitable alternative atmosphere. The drying step is preferably carried out in the initial stages of the calcining step. Drying and calcining times are not critical and depend on temperatures. These are readily determined by simple experimentation. Five minutes to ten hours are usually sufficient, although longer times are acceptable.

The amount of metals deposited upon the support are not critical and may be varied through a wide range so long as they are present in sufficient amount to be catalytically effective, a condition which is readily determined by experiment. The support will contain from about 0.1 to about 20% wt of copper measured as the metal per total weight of the catalyst, from about 0.1 to about 10% wt of zinc, measured as the metal per total weight of the catalyst and from about 0.01 to about 10% wt of chromium, measured as the metal per total weight of the catalyst.

After calcining, the catalyst is activated in a reducing environment. The reducing environment may be either a gaseous atmosphere or a suitable liquid solution. Suitable examples of a gaseous reducing atmosphere comprise hydrogen, ammonia, carbon monoxide, and the like. The preferred atmosphere is hydrogen. Activation temperatures when utilizing a gaseous atmosphere range from about 175° C. to about 550° C. The time needed for activation in a gaseous atmosphere will depend on the temperature, the higher the temperature the shorter the time and vice versa, and typically, useful times have been found to range from about 0.1 hour to about 24 hours, although times outside these limits are also useful, economic considerations, however, tending to dictate against their use. Reducing solutions are those typically used in the art, such as, for example, aqueous or ammoniacial solutions of hydrazine, sodium borohydride or formaldehyde or solutions of, for example, triethyl aluminum or di-isobutyl aluminum hydride in an organic solvent such as heptane. Temperatures utilized with reducing solutions range from about room temperature to about 100° C. or higher with times ranging from about 0.01 to about 10 hours or longer. Time and temperatures are not critical and will depend on the solution being utilized. They are readily determined by routine experimentation. Although not being stated as a limiting condition on the invention, it is believed that the activation of the catalyst in a reducing environment serves to at least partially reduce the copper from the +2 valence state to the +1 and/or 0 valence state which is believed to contribute to the catalytic activity of the catalyst. Reducing conditions, however, should not be so severe as to reduce the zinc and chromium from ZnO and $Cr_2O_3$. The appropriate activation conditions can readily be determined by experimentation. For example, times and temperatures can be varied and the resultant catalytic material can be examined by x-ray photoelectron spectroscopy in order to determine the activation state of the copper.

While the catalyst of this invention is useful for converting alcohols in general to the corresponding carbonyl compounds, it has been found that the copper-zinc-chromium/alpha-alumina supported catalyst of this invention has a high selectivity and activity for the conversion of sec-butyl alcohol to methyl ethyl ketone.

The catalyst of this invention can be utilized in fluidized beds or packed columns, preferably the latter. The sec-butyl alcohol fed to the reactor can contain minor amounts of water present, for example, up to about twenty-five percent by weight, preferably up to about fifteen percent by weight. The reactor is operated over a temperature ranging from about 200° to about 500° C., preferably from about 250° C. to about 350° C. Reactor pressure is maintained from about atmospheric to about 1000 psi, preferably from about atmospheric to about 250 psi. The alcohol is fed to the reactor at liquid hourly space velocities ranging from about 1 to about 100, preferably from about 2 to about 15.

Although hydrogen is generated in the reaction, the presence of an external supply of hydrogen is desirable to prevent the catalyst from rapidly losing activity as a function of time. It is desirable to maintain the partial pressure of hydrogen from about 5 to about 800 psi, and preferably from about 15 to about 250 in the reactor. Molar ratios of hydrogen to isopropyl alcohol of greater than about 3 are desirable.

The reaction may be conducted batchwise or in a continuous operation. By way of illustration of the batchwise process, a high pressure autoclave is charged with sec-butyl alcohol and pressurized with hydrogen and heated to reaction temperature. After the reaction is allowed to proceed for the desired length of time, the autoclave is cooled, the excess hydrogen vented, and the products worked up by conventional methods. By way of illustration of continuous operation, a vertical, high pressure column is charged with catalyst; and sec-butyl alcohol is supplied at one end of the column. At the same time hydrogen is metered into the column in cocurrent flow. During the reaction, appropriate conditions of temperature and pressure are maintained. The reaction product is removed from the bottom of the column, freed from hydrogen and worked up by conventional methods. The hydrogen is advantageously recycled to the reactor.

The process of this invention is further described by the following illustrative embodiments which are provided for illustration and are not to be construed as limiting the invention.

ILLUSTRATIVE EMBODIMENTS

Catalyst Preparation

A stock solution of metal salts is prepared by dissolving 148.10 g (0.613 moles) of $Cu(NO_3)_2.3H_2O$, 105.80 g (0.356 moles) of $Zn(NO_3)_3.6H_2O$ and 58.18 g (0.145 moles) of $Cr(NO_3)_3.9H_2O$ in enough distilled water to give 250 ml of solution. A sample of Pechiney alpha alumina having a surface area of about 9 m²/g and a pore volume of about 0.45 cc/g is ground and sieved to about 14–35 mesh. The sieved material is dried at about 950° F. for about one hour and then placed in a dessicator to cool. A 37.5 g portion of the dried alumina is impregnated with 18 ml of the stock solution. This material is dried in a vacuum oven at 120° C. for 1.5 hours, then calcined in a vycor tube in the presence of air (flow rate 610 ml/min). The temperature for the calcination is raised gradually from 125° C. to a maximum of 500° C. A 24 g (30 ml) portion of the calcined material is loaded into a stainless steel tube and reduced in a mixture of hydrogen (flow rate of 0.233 SCFH) and nitrogen (flow rate 0.572 SCFH). The reduction temperature is raised gradually from 150° C. to 500° C. The catalyst is then ready for use. An analysis of the catalyst will show it to contain about 6% w Cu, 3.6% w, Zn and 0.7% w Cr.

PROCESS

Two additional catalysts are prepared as described above using other alumina supports. One catalyst is prepared using Norton alpha alumina support (Norton SA 5556) with a surface area of about 0.2 m²/g and a pore volume of about 0.25 cc/g. The other catalyst is prepared using Kaiser gamma alumina (Kaiser KA-201) with a surface area of about 365 m²/g and a pore volume of about 0.42 cc/gm. These catalysts contain about 6% w Cu, 3.6% w Zn and 0.7% w Cr.

The above three described catalysts in addition to a commercial brass spelter catalyst are indivdually charged to a small cylindrical test reactor having a volume of 25 cc. The catalyst bed is composed of a mixture of 10 cc catalyst plus 10 cc silicon carbide inert diluent (Aluxite). The feed stock is neat sec-butyl alcohol. Hydrogen is metered into the reactor at a rate of about 100 cc/min. The results are shown in the table below.

TABLE I

| | Conversion of sec-Butyl Alcohol to Methylethyl Ketone | | | | | |
|---|---|---|---|---|---|---|
| | Temp | | Conv | Molar Selectivity, % | | |
| Catalyst | °C. | LHSV | % | Butene | MEK | Heavy Products |
| Brass Spelter | 400 | 2.3 | 73 | 3.7 | 95.9 | 3.4 |
| Cu/Zn/Cr/Kaiser A-201 γ-$Al_2O_3$ (S.A. 365 m²/g) | 375 | 10 | 93 | 28 | 66 | 0 |

TABLE I-continued

| Catalyst | Conversion of sec-Butyl Alcohol to Methylethyl Ketone | | | | | |
|---|---|---|---|---|---|---|
| | Temp °C. | LHSV | Conv % | Molar Selectivity, % | | |
| | | | | Butene | MEK | Heavy Products |
| Cu/Zn/Cr/ L.A. 5556 α-Al$_2$O$_3$ (S.A. 0.2 m$^2$/g) | 380 | 6 | 94.7 | 0.7 | 93.6 | 5.6 |
| Cu/Zn/Cr/PECHENEY SCS-9 α-Al$_2$O$_3$ (S A. 9 m$^2$/g | 380 | 6 | 93.4 | trace | 92.6 | 7.4 |

Pressure: 35-175 psig
Feed: Neat sec-butyl alcohol

We claim:

1. A process for converting sec-butyl alcohol to methylethyl ketone which comprises contacting the alcohol at a temperature ranging from about 200° C. to about 500° C. with a catalyst consisting essentially of copper, zinc and chromium supported on a porous alpha alumina support, wherein the copper measured as the metal ranges from about 0.1 to about 20 percent by weight of the total catalyst, the zinc ranges from about 0.1 to about 10 percent by weight of the total catalyst and the chromium ranges from about 0.01 to about 10 percent by weight of the total catalyst.

2. The process of claim 1 wherein the support has a surface area ranging from about 0.05 to about 50 m$^2$/g.

3. The process of claim 1 wherein the temperature ranges from about 250° C. to about 450° C.

4. The process of claim 1 wherein the pressure ranges from about 15 to about 1000 psia.

5. The process of claim 1 wherein hydrogen is additionally added.

6. The process of claim 1 wherein hydrogen is additionally added in an amount such that the molar ratio of hydrogen to alcohol is greater than about 3.

7. A process for converting sec-butyl alcohol to methylethyl ketone which comprises contacting the alcohol at a temperature ranging from about 200° C. to about 500° C. with a catalyst prepared by impregnating a porous alpha alumina support with a solution(s) of copper, zinc and chromium salts, drying the impregnated support, calcining the support in an oxidizing atmosphere at a temperature ranging from about 100° C. to about 900° C. and then activating the calcined material in a reducing environment, wherein the copper measured as the metal ranges from about 0.1 to about 20 percent by weight of the total catalyst, the zinc ranges from about 0.1 to about 10 percent by weight of the total catalyst and the chromium ranges from about 0.01 to about 10 percent by weight of the total catalyst.

8. The process of claim 7 wherein the support has a surface area ranging from about 0.05 to about 50 m$^2$/g.

9. The process of claim 7 wherein the temperature ranges from about 250° C. to about 450° C.

10. The process of claim 7 wherein the pressure ranges from about 15 to about 1000 psia.

11. The process of claim 7 wherein hydrogen is additionally added.

12. The process of claim 7 wherein hydrogen is additionally added in an amount such that the molar ratio of hydrogen to alcohol is greater than about 3.

13. The process of claim 7 wherein the reducing environment is a gaseous atmosphere and activation is made at a temperature ranging from about 175° C. to about 550° C.

14. The process of claim 7 wherein the reducing environment is a gaseous atmosphere comprising hydrogen, ammonia or carbon monoxide and activation is made at a temperature ranging from about 175° C. to about 550° C.

* * * * *